United States Patent
Daimon et al.

(10) Patent No.: US 6,582,922 B1
(45) Date of Patent: *Jun. 24, 2003

(54) METHOD OF EXTRACTING NUCLEIC ACIDS USING PARTICULATE CARRIER

(75) Inventors: Katsuya Daimon, Otsu (JP); Shigeru Komai, Otsu (JP); Yutaka Takarada, Otsu (JP)

(73) Assignee: Toyo Boseki Kabushiki Kaisha (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/067,208

(22) Filed: Feb. 7, 2002

Related U.S. Application Data

(62) Division of application No. 09/548,717, filed on Apr. 13, 2000.

(30) Foreign Application Priority Data

Apr. 14, 1999 (JP) ............................................. 11/106868

(51) Int. Cl.$^7$ ............................ C12Q 1/68; C12N 15/10; C07H 1/06; C12P 19/34
(52) U.S. Cl. ........................ 435/6; 435/91.1; 435/91.3; 536/25.4
(58) Field of Search ................................. 435/810, 91.1, 435/91.3, 6; 536/25.42, 25.4

(56) References Cited

U.S. PATENT DOCUMENTS

| 5,208,160 A | 5/1993 | Kikyotani et al. |
| 5,234,809 A | 8/1993 | Boom et al. |
| 5,520,917 A | 5/1996 | Mizuguchi et al. |
| 5,945,525 A | * 8/1999 | Uematsu et al. ......... 536/25.42 |

FOREIGN PATENT DOCUMENTS

EP 0 757 106 A2 2/1997

OTHER PUBLICATIONS

H. Saito et al., "Preparation of Transforming Deoxyribonucleic Acid by Phenol Treatment," *Biochem. Biophys. Acta*, 72 (1963), pp. 619–629.

H. Birboim. et al, "A Rapid Alkaline Extraction Procedure for Screening Recombinant Plasmid DNA," *Nucleic Acids Research*, vol. 7, No. 6, 1979, pp. 1513–1523.

B. Vogelstein et al., "Preparative and Analytical Purification of DNA from Agarose," *Proc. Natl. Acad. Sci. USA*, vol. 76, 1979, pp. 615–619.

R. Boom, et al., "Rapid and Simple Method for Purification of Nucleic Acids," *Journal of Clinical Microbiology*, 3–90, pp. 495–203.

* cited by examiner

*Primary Examiner*—Kenneth R. Horlick
*Assistant Examiner*—Cynthia B. Wilder
(74) *Attorney, Agent, or Firm*—Morrison & Foerster LLP

(57) ABSTRACT

The present invention provides a method of extracting and isolating nucleic acids from a material containing nucleic acids using a nucleic acid-binding particulate carrier. More specifically, the present invention provides a nucleic acid extraction method using a particulate carrier having a particle diameter of 0.5 to 15.0 $\mu$m, a pore diameter of 50 to 500 nm and a pore volume of 200 to 5000 mm$^3$/g. According to the method of the invention, nucleic acids can be efficiently extracted from a biological material, in particular a material containing a large amount of contaminants, such as a clinical sample.

17 Claims, No Drawings ns has been proposed (J. Clinical Microbiology 28-3:495–503, 1990, and Japanese Unexamined Patent Publication No. 289596/1990). The technique comprises mixing a sample with nucleic acid-binding silica particles and chaotropic ions capable of releasing nucleic acids contained in the sample to thereby bind the nucleic acids to silica particles, removing contaminants by washing, and collecting the nucleic acids bound to the silica particles. This technique is advantageous in that it is suitable not only for extraction of DNA but also for extraction of less stable RNA, and capable of giving high-purity nucleic acids. However, the step of washing the particles having bound nucleic acids involves centrifugation, filtration using a filter, etc., and therefore is liable to become complicated when automatized.

METHOD OF EXTRACTING NUCLEIC ACIDS USING PARTICULATE CARRIER

This application is a divisional of U.S. patent application Ser. No. 09/548,717, filed Apr. 13, 2000.

The present invention relates to a method of extracting and isolating nucleic acids from a material containing nucleic acids, using a nucleic acid-binding particulate carrier. More specifically, the present invention relates to a nucleic acid extraction method using a porous particulate carrier having a particle diameter of 0.5 to 15.0 μm, a pore diameter of 50 to 500 nm and a pore volume of 200 to 5000 mm$^3$/g.

Recent advances in the genetic engineering and molecular biology fields enable analyses of infections and genetic diseases at the DNA/RNA level. In particular, detection of a trace amount of nucleic acid, which has so far been extremely difficult, becomes readily achievable, and therefore gene analyses are remarkably facilitated, owing to the invention of nucleic acid amplification methods, such as polymerase chain reaction (PCR; Science 230:1350–1354, 1985) and nucleic acid sequence based amplification method (NASBA; Nature 350: 91–92, 1991 and Japanese Patents Nos. 2648802 and 2650159).

However, for detecting a nucleic acid in a biological sample, or amplifying a nucleic acid before detection as required, it is necessary to selectively withdraw nucleic acids from the sample, since biological samples usually contain large amount of constituents other than nucleic acids, such as proteins, lipids and saccharides, which are likely to adversely affect the amplification or detection. Accordingly, manipulations are required to remove contaminants from biological samples and to extract and isolate nucleic acids.

Various techniques have been employed for nucleic acid isolation. Typical examples include techniques in liquid phases, such as the phenol-chloroform extraction method (Biochimica et Biophysica Acta 72:619–629, 1963) and the alkaline SDS method (Nucleic Acid Research 7:1513–1523, 1979). These techniques are widely used on a laboratory scale, but require technological skills and are difficult to carry out with good reproducibility since they use organic solvents that are toxic and difficult to dispose of, such as phenol and chloroform, and use hazardous materials such as sodium hydroxide.

Nucleic acid isolation techniques utilizing nucleic acid-binding carriers include one utilizing glass particles and a sodium iodide solution (Proc. Natl. Acad. Sci. USA 76-2:615–619, 1979), and one utilizing hydroxyapatite (Japanese Unexamined Patent Publication No. 263093/1988). Although these techniques do not employ toxic organic solvents or other toxic substances, but have the problem that they are not suitable for processing many samples at a time and thus require a prolonged period of time, since they involve a number of centrifugation operations.

In short, conventional nucleic acid isolation techniques as mentioned above have the drawback that they use hazardous reagents such as organic solvents and alkalis, or involve centrifugation operations and are unsuitable for processing many samples at a time. Further, the techniques encounter large problems when the extraction and isolation steps are automated, although automatization of the extraction and isolation of nucleic acids is indispensable for processing a number of samples with good reproducibility and for reducing labor cost.

For automatization of extraction and isolation of nucleic acids, a technique utilizing silica particles and chaotropic ions has been proposed (J. Clinical Microbiology 28-3:495–503, 1990, and Japanese Unexamined Patent Publication No. 289596/1990). The technique comprises mixing a sample with nucleic acid-binding silica particles and chaotropic ions capable of releasing nucleic acids contained in the sample to thereby bind the nucleic acids to silica particles, removing contaminants by washing, and collecting the nucleic acids bound to the silica particles. This technique is advantageous in that it is suitable not only for extraction of DNA but also for extraction of less stable RNA, and capable of giving high-purity nucleic acids. However, the step of washing the particles having bound nucleic acids involves centrifugation, filtration using a filter, etc., and therefore is liable to become complicated when automatized.

For facilitating mixing and washing of the silica particles, Japanese Unexamined Patent Publication No. 19292/1997 discloses a technique comprising magnetizing the silica particles and mixing a sample with the particles utilizing the magnetic field, followed by stirring. In this technique, nucleic acids are bound to the magnetic silica particles, the particles are magnetically separated from the liquid phase, and after washing the particles, the nucleic acids are collected. The steps of the technique become simpler and easier when automatized. However, the influence of contaminants in the sample cannot be excluded by simply employing magnetized particles, and as the result, this technique often shows reduced collection efficiency.

Namely, when a sample containing a large amount of contaminants is used, contaminants in the sample cover the particle surfaces, whereby nucleic acids adsorb to the particle surfaces at a reduced adsorption rate.

To overcome the problem, Japanese Unexamined Patent Publication No. 262387/1999 proposes a technique utilizing a particulate carrier with a larger particle surface area, and Japanese Unexamined Patent Publication No. 178571/1999 proposes a technique wherein a particulate carrier is suspended in a surfactant beforehand in order to preclude adsorption of contaminants. However, it is still difficult to extract a sufficient amount of nucleic acids from samples containing a large amount of contaminants, such as whole blood samples.

The object of the present invention is to solve the above problems by providing a method for efficiently extracting and isolating nucleic acids from a material containing nucleic acids, in particular from a clinical sample or like sample containing a large amount of contaminants.

The present inventors conducted extensive research to achieve the above object, and found that a porous particulate carrier having a pore diameter of at least 50 nm and a pore volume of at least 200 mm$^3$/g is useful for efficiently extracting nucleic acids from a biological material, in particular from a clinical sample or like sample containing a large amount of impurities. The present invention has been accomplished based on this novel finding.

Porous particulate carriers have a pore diameter (i.e., diameter of the openings of the pores) and a pore volume (i.e., interior volume of the pores). The present invention has been accomplished based on the finding that the pore diameter and the pore volume affect the collection efficiency of nucleic acids from a sample.

The present invention provides a method of extracting nucleic acids from a material containing nucleic acids using a nucleic acid-binding particulate carrier, wherein the particulate carrier has a particle diameter of 0.5 to 15.0 μm, a pore diameter of 50 to 500 nm and a pore volume of 200 to 5000 mm$^3$/g.

Specifically, the present invention provides a method of extracting nucleic acids from a material containing nucleic acids, the method comprising the following steps (a) to (c):

(a) mixing the material containing nucleic acids, a nucleic acid-binding particulate carrier having a particle diameter of 0.5 to 15.0 µm, a pore diameter of 50 to 500 nm and a pore volume of 200 to 5000 mm³/g, and a nucleic acid extraction solution for allowing the nucleic acids to adsorb to the particulate carrier, to thereby bind the nucleic acids to the particulate carrier;

(b) separating a composite of the nucleic acids and the particulate carrier from the mixture obtained in Step (a) to remove contaminants; and (c) eluting and collecting the nucleic acids from the composite of the nucleic acids and the particulate carrier.

The present invention also provides a nucleic acid extraction kit comprising a nucleic acid-binding particulate carrier having a particle diameter of 0.5 to 15.0 µm, a pore diameter of 50 to 500 nm and a pore volume of 200 to 5000 mm³/g, a nucleic acid extraction solution for allowing the nucleic acids to adsorb to the carrier, and a nucleic acid eluate for eluting the nucleic acids from a composite of the nucleic acids and the particulate carrier.

The present invention further provides a nucleic acid detection method comprising extracting nucleic acids by the above method, amplifying a target nucleic acid by amplification reaction and detecting the target nucleic acid.

The following are definitions of terms used herein and descriptions of measurement methods employed herein.

Nucleic Acid-binding Particulate Carrier

The term "nucleic acid-binding particulate carrier" means a particulate carrier capable of binding or adsorbing nucleic acids to the particle surfaces.

The particulate carrier for use in the invention is porous, and "pores" of the particulate carrier are minute cavities on the particle surfaces, and "pore volume" means the interior volume of the pores. "Pore diameter" means the diameter of the openings of the pores present on the carrier, and, as used herein, is intended to mean the average diameter of the pores, since a pore diameter of a fine powder usually indicates the average pore diameter. "Particle diameter" indicates the diameter of particles, assuming that the particles are spherical.

In the present invention, the pore diameter and pore volume of the particulate carrier are analyzed by mercury penetration. Mercury penetration is an analysis based on the physical principle that mercury wets substantially no porous substances on their pore walls, and thus does not penetrate into the pores unless being pressurized. In this analysis, mercury surrounding the analyte is uniformly pressurized from the periphery. As the pressure gradually increases, mercury penetrates first into pores with a relatively large diameter and then gradually into pores with a smaller diameter. Assuming that there is a pore having a cylindrical shape and a radius of r, the force ($\pi r^2 P$) of penetration of mercury into the pore when applying a pressure P and the force ($-2\pi r \times \gamma \cos \theta$) of repulsion towards mercury are in equilibrium. Thus, mercury penetrates into pores having a radius greater than the radius r calculated according to the following equation:

$$Pr = -2\gamma \cos \theta \quad (1)$$

wherein P is the pressure, r is the pore radius, γ is the surface tension of mercury, θ is the contact angle of mercury and the analyte (90° C.<θ180° C.). The above equation (1) is called Washburn equation, and the value of the right side thereof is a constant which is characteristic of the analyte and is equal to the penetration amount of mercury relative to the pressure or the pore radius. The penetration amount of mercury indicates the cumulative volume of pores having a radius greater than the radius r.

The particle diameter is measured by a particle size distribution measuring method utilizing the difference in the rates of precipitation of particles with different diameters in a solution.

It is essential in the present invention that the particulate carrier has a pore diameter of at least 50 nm and a pore volume of at least 200 mm³/g. Use of a particulate carrier having a larger pore diameter and a larger pore volume makes it possible to collect an increased amount of nucleic acids. If the particulate carrier has a pore diameter less than 50 nm or a pore volume less than 200 mm³/g, there arises the problem that nucleic acids are not bound or adsorbed to the particle surfaces, owing to the influence of contaminants in the sample, or other factors. However, particulate carriers having a pore diameter greater than 500 nm and/or a pore volume greater than 5000 mm³/g are not preferable, since a large amount of constituents other than nucleic acids is presumably liable to be collected in the particles, owing to the excessive spaces in the pores. Further, particles having a pore diameter greater than 500 nm are likely to be brittle and fail to maintain their structure, since the pore diameter occupies a considerable part of the pore diameter. The pore diameter is preferably 50 to 500 nm, more preferably 50 to 300 nm particularly preferably 80 to 250 nm. The pore volume is preferably 200 to 5000 mm³/g, more preferably 300 to 3000 mm³/g.

If having a particle diameter less than 0.5 µm, the particulate carrier has excessively high dispersibility, and is difficult to collect for washing or the like. If the particle diameter is larger than 15.0 µm, the particulate carrier has a high density and therefore rapidly precipitates from the mixture, hence undesirable. The particle diameter is preferably 0.5 to 15.0 µm, more preferably 0.5 to 10.0 µm, particularly preferably 1.0 to 5.0 µm.

For example, during formation of a composite of nucleic acids and the magnetic silica particulate carrier, contaminants derived from organisms tend to adhere to the particle surfaces of the magnetic silica particulate carrier and prevent binding of nucleic acids, when blood or like biological sample containing a large amount of contaminants is used. That is, the greater the amount of contaminants, the lower the nucleic acid collection efficiency becomes. For solving this problem, the method of the invention employs a specific particulate carrier which is large in pore diameter and pore volume, so that even if contaminants in the sample adhere to the carrier, they are less likely to affect the binding of nucleic acids. Therefore, the method of the invention achieves a high collection efficiency.

Accordingly, it is necessary in the method of the present invention to use a particulate carrier having a pore diameter of 50 to 500 nm, a pore volume of 200 to 5000 mm³/g and a particle diameter of 0.5 to 15.0 µm.

The term "surface area" as used herein means the total of the surface areas of the particles of the carrier. It is a common practice to express the surface area of a fine powder in a surface area per unit weight (e.g., 1 g), not in a surface area per particle. The surface area per unit weight is called specific surface area. Further, "outer surface area" means the area of the outer surface of the particles of the carrier and is expressed as an outer surface area per unit weight (e.g., 1 g), like the surface area.

In the present invention, the surface area and specific surface area are measured by mercury penetration and gas absorption. The outer surface area of the particulate carrier is found by subtracting the surface area inside the particles from the surface area. The surface area inside the particles is calculated from the pore volume.

Consideration is then given to the specific surface area S of pores. Assuming that there are a number n of cylindrical pores having a radius of r and a depth of l, the increase in specific surface area is:

$$dS=2\pi rl \times n \qquad (2)$$

and the increase in pore volume is:

$$dV=\pi r^2 l \times n \qquad (3).$$

From the equations (2) and (3), $$dS=(2/r)dV.$$

Thus, the specific surface area $S=(2/r)\int dV$.

The outer surface area of the particulate carrier is usually at least 5 m²/g, preferably 5 to 500 m²/g, more preferably 20 to 400 m²/g.

The specific surface area of the particulate carrier is usually 5 to 800 m²/g, preferably 10 to 600 m²/g, more preferably 15 to 500 m²/g.

It is preferred that the particulate carrier for use in the present invention comprises silica or its derivative, and it is more preferred that the particulate carrier be magnetic carrier. As used herein, the term "silica" sometimes means "silica or its derivative".

As used herein, the term "silica or its derivative" includes $SiO_2$ crystals and silicon oxides of other forms, skeletons of diatomaceous earth composed of $SiO_2$, and amorphous silicon oxides.

"Magnetic" indicates capability of being temporarily magnetized by a permanent magnet and attracted to the magnet. Magnetic particulate carriers can be easily separated from a solution phase.

It is more desirable that the particulate carrier for use in the present invention be magnetic particulate carrier comprising silica or its derivative (hereinafter referred to as "magnetic silica particulate carrier"). It is particularly desirable that the particles of magnetic silica particulate carrier be composites of fine particles each comprising a superparamagnetic metal oxide covered with silica, the composites having porous surfaces. The particles of the magnetic silica particulate carrier are substantially complete spheres. Nucleic acids are bound to the silica particulate carrier via hydrogen bonds formed between hydroxyl groups on the particle surfaces of the carrier and bases of the nucleic acids.

Superparamagnetic metal oxides are metal oxides that are responsive to a magnetic field variation but are not permanently magnetized, and have a small residual magnetization. The particle size of the superparamagnetic metal oxide for use in the invention is about 10 to 200 nm, preferably about 20 to 100 nm. Preferred superparamagnetic metal oxides include iron oxides such as triiron tetraoxide ($Fe_3O_4$) and γ-type iron sesquioxide ($\gamma$-$Fe_2O_3$) obtainable by gradually oxidizing triiron tetraoxide. Triiron tetraoxide has small residual magnetization and a preferred surface structure (substantially complete spheres), so that it can be used repeatedly by magnetic separation and redispersion. Magnetic silica particulate carriers containing triiron tetraoxide are stable in weakly acidic aqueous solutions and can be stored over a period of 2 years or more.

The magnetic silica particulate carrier for use in the invention contains the superparamagnetic metal oxide in a proportion of preferably 10 to 60 wt. %, more preferably 20 to 40 wt. %, although depending on the strength of the magnetic force. When containing the superparamagnetic metal oxide in a proportion within the specified range, the magnetic silica particulate carrier can be readily separated using a commercially available magnet.

For use in the invention, a particulate carrier having the following properties is most preferred:
(1) being magnetic silica particles containing a superparamagnetic iron oxide,
(2) having an outer surface area of at least 5 m²/g,
(3) comprising composites of fine particles each comprising a superparamagnetic metal oxide covered with silica, the composites having porous surfaces,
(4) having a superparamagnetic iron oxide content of 10 to 60 wt. %,
(5) having a specific surface area of 5 to 800 m²/g,
(6) having a pore diameter of 50 to 500 nm,
(7) having a pore volume of 200 to 5000 mm³/g, and
(8) having a particle diameter of 0.5 to 15.0 μm.

Process for Production of Particulate Carrier

The particulate carrier for use in the invention can be produced by a known process disclosed in, for example, Japanese Unexamined Patent Publication No. 47273/1994.

For example, a magnetic silica particulate carrier containing an iron oxide can be produced by the following process. First, triiron tetraoxide is added to an alcohol solution of tetraethoxysilane, and dispersed and wetted using an ultrasonic dispersion apparatus. A catalyst for hydrolyzing tetraethoxysilane is added to the dispersion and ultrasonically dispersed so as to deposit silica on the particle surfaces of triiron tetraoxide. Sodium silicate is added to the resulting dispersion, and an organic solvent and a surfactant (a toluene solution of sorbitan monostearate) are added to form a w/o emulsion. The emulsion is added to an aqueous solution of ammonium sulfate, followed by thorough stirring. The resulting mixture was subjected to filtration separation, washing with water, alcohol precipitation and drying, to thereby obtain desired spherical silica particles.

Nucleic Acid Extraction Method Using Nucleic Acid-binding Particulate Carrier

In the method of the invention, the nucleic acid-binding particulate carrier having the above properties is used to extract nucleic acids from a material containing nucleic acids. Specifically, nucleic acids are extracted by contacting a nucleic acid-binding particulate carrier having the above properties with a material containing nucleic acids so that the nucleic acids are bound and adsorbed to the carrier.

More specifically, according to the method of the invention, nucleic acids are extracted and isolated by the steps of:
(a) mixing a material containing nucleic acids, a nucleic acid-binding particulate carrier having a particle diameter of 0.5 to 15.0 μm, a pore diameter of 50 to 500 nm and a pore volume of 200 to 5000 mm³/g, and a nucleic acid extraction solution for allowing the nucleic acids to adsorb to the carrier, to thereby bind the nucleic acids to the carrier (adsorption step);
(b) separating a composite of the nucleic acids and the particulate carrier from the mixture obtained in Step (a) to remove contaminants (separation step); and
(c) eluting and collecting the nucleic acids from the composite (elution step).

Step (a)

The material containing nucleic acids for use in the invention may be a biological material, specifically, an animal-derived biological material such as blood (including whole blood, blood serum, blood plasma, etc.), urine, saliva or like body fluid, or a material derived from organisms other than animals, such as plants and microorganisms. The material for use in the invention may also be cells separated from the above organisms, cultures of said cells, or partially purified nucleic acids.

According to the present invention, the nucleic acids may be DNA or RNA. DNA may be double-stranded DNA, single-stranded DNA, plasmid DNA, genomic DNA, cDNA, etc. RNA may be RNA derived from exogenous parasites such as virus, bacteria and fungi, or endogenous RNA derived from organisms that produce these biological materials. Thus, RNA may be tRNA, mRNA, rRNA, etc.

The nucleic acid extraction solution for use in the invention is a solution capable of destroying nucleic acid-containing cells in the biological material to thereby expose the nucleic acids and allow the nucleic acids to bind to the particulate carrier. Preferred examples of such solutions include those containing substances capable of increasing hydrophobicity of the surfaces of glass or slica particles, such as chaotropic substances.

Specific examples of chaotropic substances include guanidine salt, potassium iodide, sodium iodide, (iso) thiocyanate sodium perchlorate and urea, and more specifically, guanidine thiocyanate, guanidine hydrochloride, sodium iodide, potassium iodide, sodium perchlorate and urea. Among these chaotropic substances, guanidine thiocyanate and guanidine hydrochloride can be preferably used since they have high inhibitory activity against ribonucleases that decompose RNA. Thus, the nucleic acid extraction solution is preferably an aqueous solution of a compound having inhibitory activity against nucleases, such as guanidine thiocyanate and/or guanidine hydrochloride. The concentration of the chaotropic substance in the nucleic acid extraction solution is usually 1.0 to 8.0 M, preferably 4.0 to 7.0 M, although depending on the kind of the chaotropic substance used. For example, guanidine hydrochloride, when employed, is used preferably at a concentration of 4.0 to 7.5 M. When employing guanidine thiocyanate, it is used preferably at a concentration of 3.0 to 5.5 M.

The nucleic acid extraction solution for use in the invention preferably contains a buffer. The buffer may be added to the extraction solution before use, or may be added as a buffer solution to the solution after dissolution of cells. Conventional buffers can be used in the invention without limitation. Preferred are those showing buffer action at neutral pH values, i.e., pH 5.0 to 9.0. Useful examples include Tris-hydrochloride, sodium tetraborate-hydrochloric acid, potassium dihydrogenphosphate-sodium tetraborate. Preferably, the buffer is used at a concentration of 1 to 500 mM in the nucleic acid extraction solution, and has a pH value of 6.0 to 9.0.

The nucleic acid extraction solution may contain a surfactant to destroy cell membranes or denature proteins in cells. Surfactants conventionally used for nucleic acid extraction from cells or the like may be employed without limitation. Specific examples include nonionic surfactants such as Triton surfactants and Tween surfactants, and anionic surfactants such as N-lauroyl sarcosine sodium. According to the invention, it is particularly preferred to use a nonionic surfactant at a concentration of 0.1 to 2.0 wt. % in the nucleic acid extraction solution. A anionic surfactant, when employed, is preferably used at a concentration similar to that of the nonionic surfactant.

Further, it is desirable that the nucleic acid extraction solution contains a suitable amount of a reducing agent such as 2-mercaptoethanol or dithiothreitol, in order to denature and inactivate proteins, in particular ribonucleases, contained in the sample.

The particulate carrier is usually used as suspended in sterilized water, a 1 mM to 5 M NaCl solution, a 1 mM to 5 M LiCl solution or like solution.

According to the invention, relative to 0.01 to 2 ml of a sample containing nucleic acids, the particulate carrier is used usually 0.5 to 10 mg, preferably 2 to 5 mg, and the nucleic acid extraction solution is used usually 0.09 to 9 ml, preferably 0.9 to 2 ml, although depending on the nucleic acid concentration of the sample. It should be noted, however, that the amounts of the particulate carrier and the nucleic acid extraction solution are not limited to the above ranges.

In the invention, the particulate carrier and a material containing nucleic acids are mixed with the nucleic acid extraction solution so that the nucleic acids are contacted with and adsorbed to the nucleic acid-binding particulate carrier, giving a composite of the particulate carrier and the nucleic acids.

To achieve thorough mixing, stirring can be carried out by vortex action, end-over-end action or magnetic action, for about 1 to 60 minutes. By stirring, nucleic acids, small amounts of proteins and saccharides in the sample are adsorbed to the nucleic acid-binding particulate carrier. The temperature for stirring is not limited.

Step (b)

The mixture obtained in Step (a) is separated into a solution containing contaminants unbound to the particulate carrier and the particulate carrier having nucleic acids bound thereto.

The separation can be carried out by centrifugation. Alternatively, when a magnetic particulate carrier is used, magnetic separation using a magnet or the like can be carried out with ease. The solution containing contaminants are removed by the separation.

After removing the solution containing contaminants, the particulate carrier may be washed with a washing solution as required, to elute unnecessary substances such as proteins, saccharides and lipids.

The washing solution is not limited, as long as it does not cause elution of nucleic acids from the particulate carrier and is capable of eluting proteins, saccharides and lipids from the carrier. Preferably, the carrier is washed with a solution containing a chaotropic substance and/or an alcohol solution. As a chaotropic substance, at least one compound selected from the group consisting of guanidine thiocyanate, guanidine hydrochloride and sodium thiocyanate is preferred. More preferred is a 4.0 to 7.5 M guanidine hydrochloride solution. A preferred alcohol solution is a 40 to 100%, preferably 60 to 100% alcohol solution. Usable alcohols include ethanol, propanol, isopropanol and butanol, among which ethanol is preferred. In particular, it is desirable to wash the carrier with a solution containing a chaotropic substance, preferably with a solution similar to the nucleic acid extraction solution used in Step (a), since said extraction solution is effective for removing lipids, saccharides and proteins, and then it is desirable to wash the carrier with a 40 to 100% ethanol solution. When employing alcohol solutions, use of two alcohol solutions with different concentrations is more effective. For example, the carrier can be washed with a 70% ethanol solution and then with a 99% ethanol solution. The washing is carried out once or twice.

As required, the carrier with bound nucleic acids is dried by, for example, heating.

Step (c)

Nucleic acids are eluted using a nucleic acid eluate, from the particulate carrier obtained in Step (b), which has nucleic acids bound (adsorbed) thereto.

The nucleic acid eluate for use in the invention is not limited as long as it is capable of eluting nucleic acids from the carrier. Preferred examples include water and TE buffer solution (10 mM Tris-hydrochloride, 1.0 mM EDTA; pH 8.0).

Specifically, the nucleic acid eluate is mixed with the carrier having the nucleic acids, and the mixture is allowed to stand or stirred, to elute the nucleic acids from the carrier. The reaction temperature is about 10 to 50° C. and the reaction time is about 1 to 60 minutes. The amount of the eluate to be added is about 0.01 to 0.2 ml, preferably about 0.05 to 0.15 ml, per 1 to 50 mg of the particulate carrier.

Thereafter, the nucleic acid-containing solution is isolated from the carrier by centrifugation, or by magnetic separation using a magnet or the like when a magnetic particulate carrier is used.

Nucleic Acid Detection Method

The nucleic acid solution obtained in Step (c) need not be desalted as by dialysis or ethanol precipitation, or condensed, and can be subjected directly to enzyme reaction using a restriction enzyme, a DNA polymerase or the like. The target nucleic acid can be amplified by polymerase chain reaction (PCR) or nucleic acid sequence based amplification (NASBA) before detection by, for example, nucleic acid hybridization assay, using nucleic acid probes.

PCR can be carried out by, for example, the method described in Science 230:1350–1354, 1985. NASBA can be carried out by, for example, the method described in Nature 350:91–92, 1991, and Japanese Patents Nos. 2648802 and 2650159.

Nucleic acid hybridization assay can be carried out by the method described in, for example, Unexamined Japanese Patent Publication No. 189794/1994.

Nucleic Acid Extraction Kit

The nucleic acid extraction kit of the invention comprises at least the nucleic acid-binding particulate carrier, the nucleic acid extraction solution and the nucleic acid eluate. More specifically, the extraction kit of the invention comprises at least (1) a nucleic acid-binding particulate carrier having a particle diameter of 0.5 to 15.0 μm, a pore diameter of 50 to 500 nm and a pore volume of 200 to 5000 mm$^3$/g, (2) the nucleic acid extraction solution for allowing nucleic acids to adsorb to the carrier, and (3) the nucleic acid eluate for eluting nucleic acids. The amounts of the components (1) to (3) can be selected according to the purpose of use, and may be, for example, about 1 to 200 μl of the component (1) (the concentration of the carrier being about 0.01 to 1 g/ml), about 0.1 to 10.0 ml of the component (2) and about 10 to 500 μl of the component (3).

EXAMPLES

The following examples are provided to illustrate the invention in further detail and should not be construed to limit the scope of the claims of the invention.

Example 1

(Extraction of Nucleic Acids from Sample)

Used were four types of magnetic silica particulate carriers (products of Suzuki Yushi Industries Co., Ltd.) containing triiron tetraoxide, which were different from one other in pore diameter and pore volume. Their pore diameters ranged from about 1 to 200 nm and their pore volumes ranged from about 40 to 2200 mm$^3$/g. Of these carriers, Carriers A and B had the properties specified in the present invention, whereas Carriers C and D were conventional carriers having pore diameters and pore volumes smaller than those specified in the present invention. Carriers A to D had average particle diameters between 1.0 and 5.0 μm and contained triiron tetraoxide particles in a proportion of 30 wt. %.

The carriers were used as dissolved in a 5.0 M NaCl solution at a concentration of 0.1 g/ml. Table 1 shows the properties of Carriers A to D measured by the methods described hereinbefore.

TABLE 1

|  | Carrier A | Carrier B | Carrier C | Carrier D |
| --- | --- | --- | --- | --- |
| Pore diameter (nm) | 193.0 | 98.0 | 1.08 | 2.12 |
| Pore volume (mm$^3$/g) | 418.0 | 2119.0 | 116.0 | 41.7 |
| Average particle diameter (μm) | 4.80 | 1.88 | 4.80 | 3.06 |
| Outer surface area (m$^2$/g) | 30< | 30< | 10.74 | 23.23 |
| Specific surface area (m$^2$/g) | 250< | 250< | 224.30 | 50.31 |

A whole blood sample positive for *Vibrio parahaemolyticus* producing Thermostable Direct Haemolysin (TDH), which is a thermostable toxin, was used as a biological material. As the nucleic acid extraction solution, a solution having the following makeup was used:

50 mM Tris-HCl (pH 6.5)

5.0 M Guanidine thiocyanate 20 mM EDTA 1.2% Polyethylene glycol mono-p-isooctylphenyl ether The procedure of this Example was as follows:

(1) 0.9 ml of the nucleic acid extraction solution with the above makeup was placed into each of four 1.5 ml Eppendorf tubes, and then 0.1 ml of the whole blood sample was placed into each of the tubes, followed by thorough stirring.

(2) 50.0 μl of a suspension of each carrier in a 5.0 M NaCl solution was placed into each tube, and the resulting mixtures were thoroughly stirred and allowed to stand at room temperature for 10 minutes. While being allowed to stand, the mixtures were stirred for 5 to 60 seconds at two minute intervals.

(3) The mixtures were centrifuged at 12000 rpm for 1 minute using a centrifuge, so as to precipitate the carriers to the bottom of the tubes.

(4) The solution phases were gently removed by suction using a filter tip or a disposable syringe.

(5) 1.0 ml of a 50 mM Tris-hydrochloric acid buffer solution containing 5.0 M sodium thiocyanate was placed into each tube as a washing solution, followed by stirring. The resulting mixtures were centrifuged in the same manner as in Step (3).

(6) The solution phases were removed in the same manner as in Step (4) and the remaining contents of the tubes were washed in the same manner as in Steps (5) and (4).

(7) Each of the carriers having nucleic acids adsorbed thereto was washed in the same manner as Steps (4) and (5) using 1.0 ml of a 70% ethanol solution, and the resulting high-concentration salt solutions were removed.

(8) Each carrier was washed again with 1.0 ml of a 70% ethanol solution and then with 1.0 ml of a 99% ethanol solution in the same manner as in Step (7).

(9) The tubes were set on a heat block at 56.0° C. and allowed to stand for about 30 minutes to thereby completely evaporate ethanol from the inside of the tubes and from the particulate carriers.

(10) 0.1 ml of sterilized water was placed into each of the tubes, and the tubes were set on a heat block at 56.0° C. and allowed to stand for 10 minutes.

(11) The carriers were precipitated to the bottom of the tubes by 5-minute centrifugation at 12000 rpm, and the solution phases were suctioned using a filter tip and separately placed in other tubes. The amount of each of the obtained nucleic acid solutions was 60 to 70 µl.

Example 2
(Amplification of *Vibrio parahaemolyticus* TDH Gene)

The *Vibrio parahaemolyticus* TDH gene in the solutions obtained in Example 1 was amplified by NASBA (Nature 350:91–92, 1991 and Japanese Patents Nos. 2648802 and 2650159). For the amplification, primers having the optimal sequences from *Vibrio parahaemolyticus* TDH gene were used. The 5'-end primer had a base sequence 5'-CCCCGGTTCT GATGAGATAT TGTT-3' (SEQ ID NO: 1), and the 3'-end primer had a base sequence 5'-AATTCTAATA CGACTCACTA TAGGGAGACC AATATATTAC CACTACCACT A-3' (SEQ ID NO: 2, comprising a promoter sequence for T7-RNA polymerase). The primer sequences are disclosed in Japanese Unexamined Patent Publication No. 20299/1992 and Gene 93:9–15, 1993. Also, T7-RNA polymerase, reverse transcriptase and RNaseH (ribonuclease that does not hydrolyze single- or double-stranded RNA or DNA but hydrolyzes RNA in RNA-DNA hybrids) were used in NASBA.

NASBA was carried out by the following process to obtain the target nucleic acid at a high concentration. First, 5.0 µl of each of the TDH gene nucleic acid solutions obtained by the extraction and isolation in Example 1 was separately added to 10.0 µl of an amplification solution having the makeup shown below. The resulting mixtures were allowed to stand at 65° C. for 5 minutes. Then, the reaction temperature was decreased to 41° C., and 5.0 µl of an enzyme solution having the makeup shown below was added to each of the mixtures. The resulting solutions were allowed to stand at 41° C. for 90 minutes.

The makeup of the amplification solution was as follows:
40.0 ml Tris-HCl (pH 8.5)
12.0 mM Mgcl$_2$
70.0 mM KCl
5.0 mM DTT (dithiothreitol)
15% (v/v) DMSO (dimethylsulfoxide)
1.0 mM dNTP
2.0 mM rNTP
0.2 µM primer×2

The makeup of the enzyme solution was as follows:
0.1 U RNase H
40.0 U T7-RNA polymerase
8.0 U Reverse transcriptase
0.1 g/l BSA (bovine serum albumin)

Example 3
(Detection of Amplified Nucleic Acid)

The solutions containing the amplified nucleic acid thus obtained were subjected to detection of *V. parahaemolyticus* TDH gene by sandwich hybridization assay to evaluate the collected nucleic acid amount.

[Synthesis of Capture Probe and Detection Probe for TDH Gene Detection]

A capture probe and a detection probe were synthesized by the phosphoamidite method using DNA Synthesizer Model 391 (Applied Biosystems). The capture probe had a base sequence 5'-CGGTCATTCT GCTGTGTTCG TAAAAT-3' (SEQ ID NO: 3), and the detection probe had a sequence 5'-CAGGTACTAA AXGGTTGACA TCCT-3' (SEQ ID NO: 4). In the sequence of the detection probe, X is uridine having a linker arm nucleotide at the 5'-position. These probes are disclosed in Japanese Unexamined Patent Publication No. 20299/1992 and Gene 93:9–15, 1993.

[Enzyme (Alkaline Phosphatase) Labeling of Detection Probe]

Alkaline phosphatase was bound to the synthesized detection probe via the linker arm by the method described in Nucleic Acids Research 14:6155, 1986.

[Binding of Capture Probe to Solid Phase]

A polystyrene microtiter plate (Microlite 2, Dynatec Corp.) was used as the solid phase. Each well of the plate was filled with 100 µl of the capture probe solution (25 nM) obtained above, and incubated overnight at 25° C. to bind the capture probe to the plate. The wells were then blocked with deoxyribonucleotide triphosphate.

[Detection of Nucleic Acid by Sandwich Hybridization Assay]

Using the reagents and nucleic acid solutions thus obtained, the target nucleic acid was detected by the following procedure:

Each of the nucleic acid solutions was diluted with a sodium hydroxide solution for denaturation, giving $10^{-5}$, $10^{-4}$ and $10^{-3}$ dilutions. Into each well of the above plate were placed 2.0 µl of one of the dilutions, 50.0 µl of a hybridization buffer (5×SSC (pH 7.0), 0.5% PVP, 10 mM MgCl$_2$, 1 mM ZnCl$_2$) solution and 50.0 µl of the alkaline phosphatase-labeled probe solution (0.5 nM), followed by hybridization at 50° C. for 30 minutes. Then, the liquid phase was removed from the wells, and the wells were washed with 200 µl of a first washing solution containing 1.0% sodium lauryl sulfate and 2×SSC (pH 7.0) at 50° C. for 5 minutes, then with a second washing solution containing 0.5% polyethylene glycol mono-p-isooctylphenyl ether and 2×SSC (pH 7.0) at room temperature for 5 minutes, and further with 200 µl of a 1×SSC solution. Thereafter, 100 µl of Lumiphos 480 (Wako Pure Chemical Industries, Ltd., a substrate of alkaline phosphatase) was placed into the wells to carry out enzyme reaction at 37° C. for 15 minutes. Then, the amount of luminescence was determined using Microlite 1000 (Dynatec Corp.). Table 2 shows the results of Examples 1 to 3.

TABLE 2

| Dilution | Carrier A | Carrier B | Carrier C | Carrier D |
| --- | --- | --- | --- | --- |
| $10^{-5}$ | 14.2 | 23.9 | 0.7 | 0.6 |
| $10^{-4}$ | 28.7 | 81.1 | 4.3 | 0.5 |
| $10^{-3}$ | 665.1 | 1992.1 | 43.1 | 44.5 |

Unit: Amount of luminescence (rlu)

As is apparent from Table 2, when using Carriers A and B of the invention, the detection values were remarkably higher than those obtained using conventional Carriers C and D. In particular, the detection values of the solutions of high nucleic acid concentrations ($10^{-3}$ dilutions) were significantly high. Moreover, in the detection at low nucleic acid concentrations ($10^{-5}$ dilutions), signals were detected from the solutions obtained using Carriers A and B, while the signals from the solutions obtained using Carriers C and D were substantially equivalent to those from a blank solution (1.0 rlu or less), demonstrating that the Carriers A and B are different from Carriers C and D in detection sensitivity.

Example 4
(Comparison of Nucleic Acid Recovery Rate)

A solution of the TDH gene amplified in the same manner as in Example 2 (NASBA) was added to both of a TDH gene-negative blood serum sample and a TDH-negative whole blood sample. The resulting mixtures were used as materials containing nucleic acids.

Using the thus obtained materials and Carriers A to D, nucleic acid extraction was carried out in the same manner as in Example 1 and the TDH gene was detected in the same manner as in Example 3.

The detected amount of the nucleic acid was divided by the amount of the nucleic acid added to each sample to find the nucleic acid recovery rate. Each sample was subjected to two trials of this test using each carrier.

The results are shown in Table 3.

TABLE 3

|  | Carrier A | Carrier B | Carrier C | Carrier D |
| --- | --- | --- | --- | --- |
| Blood serum sample (1st trial) | 65.1 | 64.3 | 24.9 | 31.0 |
| Blood serum sample (2nd trial) | 64.4 | 58.7 | 29.3 | 26.9 |
| Whole blood sample (1st trial) | 30.9 | 31.1 | 3.92 | 1.93 |
| Whole blood sample (2nd trial) | 25.5 | 36.9 | 2.56 | 1.51 |

Nucleic acid recovery = amount of nucleic acid recovered using each carrier/amount of nucleic acid added to each sample As is apparent from Table 3, the particulate carriers of the invention achieved remarkably high rate of nucleic acid recovery. When using the blood serum sample, Carriers A and B of the invention achieved recovery rates about twice greater than those of conventional particulate carriers (Carriers C and D). Further, when using the whole blood sample, the two carriers of the invention showed recovery rates about an order of magnitude greater than those of conventional carriers, demonstrating high efficiency of the carriers according to the present invention.

As discussed above, nucleic acids can be extracted and isolated from a biological material at a high recovery rate by using a nucleic acid-binding particulate carrier having a pore diameter of 50 to 500 nm, a pore volume of 200 to 5000 mm$^3$/g and a particle diameter of 0.5 to 15.0 μm. In particular, in extraction of nucleic acids from a material containing a large amount of contaminants, such as a whole blood sample, the particulate carrier according to the invention achieves remarkable results as compared with conventional particulate carriers.

What is claimed is:

1. A kit for extracting nucleic acids, comprising a nucleic acid-binding particulate carrier having a particle diameter of 0.5 to 15.0 μm, a pore diameter of 80 to 250 nm and a pore volume of 20 to 5000 mm$^3$/g, a nucleic acid extraction solution for adsorbing nucleic acids to the particulate carrier, and a nucleic acid eluate for eluting the nucleic acids from a composite of the nucleic acids and the particulate carrier.

2. A kit according to claim 1 wherein the particulate carrier contains silica or its derivative.

3. A kit according to claim 2 wherein the particulate carrier containing silica or its derivative is a magnetic particulate carrier.

4. A kit according to claim 3 wherein the magnetic particulate carrier contains a superparamagnetic metal oxide.

5. A kit according to claim 4 wherein the particulate carrier contains, as a superparamagnetic metal oxide, 10 to 600 wt. % of an iron oxide relative to the total weight of the particulate carrier.

6. A kit according to claim 1 wherein the particulate carrier has an outer surface area of at least 5 m$^2$/g.

7. A kit according to claim 1 wherein the particulate carrier has a specific surface area of at least 5 to 800 m$^2$/g.

8. A kit according to claim 1 wherein the nucleic acid extraction solution contains a chaotropic substance.

9. A kit according to claim 8 wherein the chaotropic substance is at least one compound selected from the group consisting of guanidine salt, potassium iodide, sodium iodide, (iso)thiocyanate, sodium perchlorate and urea.

10. A kit according to claim 8 wherein the chaotropic substance is guanidine thiocyanate and/or guanidine hydrochloride.

11. A kit according to claim 1 further comprising a first washing solution containing a chaotropic substance and a second washing solution containing an alcohol.

12. A kit according to claim 11 wherein the first washing solution contains as a chaotropic substance at least one compound selected from the group consisting of guanidine thiocyanate, guanidine hydrochloride and sodium thiocyanate.

13. A kit according to claim 12 wherein the second washing solution contains an alcohol at a concentration of 40 to 100%.

14. A kit according to claim 1 further comprising a washing solution containing ethanol at a concentration of 70% and a washing solution containing ethanol at a concentration of 99%.

15. A kit according to claim 1 wherein the nucleic acid eluate is water.

16. A kit according to claim 1 wherein the nucleic acid eluate is TE buffer solution.

17. A kit according to claim 2 the silica particulate carrier is to be bound with nucleic acids via hydrogen bonds formed between hydroxyl groups on the particle surfaces of the carrier and bases of the nucleic acids.

* * * * *

UNITED STATES PATENT AND TRADEMARK OFFICE
CERTIFICATE OF CORRECTION

PATENT NO. : 6,582,922 B1
APPLICATION NO. : 10/067208
DATED : June 24, 2003
INVENTOR(S) : Katsuya Daimon et al.

It is certified that error appears in the above-identified patent and that said Letters Patent is hereby corrected as shown below:

Col. 15, in Claim 1, line 4, delete "20" and insert --200--.

Col. 15, in Claim 5, line 3, delete "600" and insert --60--.

Signed and Sealed this

Twenty-seventh Day of May, 2008

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: comprising
      a sequence complementary to nucleotides 102-125 of the nucleotide
      sequence of V. parahaemolyticus TDH (Thermostable Direct
      Haemolysin) gene.

<400> SEQUENCE: 1
ccccggttct gatgagatat tgtt                                              24

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: comprising
      a sequence complementary to nucleotides 495-518 of the nucleotide
      sequence of V. parahaemolyticus TDH (Thermostable Direct
      Haemolysin) gene, and a promoter sequence for T7-RNA polymerase.

<400> SEQUENCE: 2
aattctaata cgactcacta tagggagacc aatatattac cactaccact a                51

<210> SEQ ID NO 3
<211> LENGTH: 26
<212> TYPE: DNA
```

-continued

```
<213> ORGANISM: Artificial Sequence
<220> FEATURE:
<223> OTHER INFORMATION: Description of Artificial Sequence: comprising
      a sequence complementary to nucleotides 339-364 of the nucleotide
      sequence of V. parahaemolyticus TDH (Thermostable Direct
      Haemolysin) gene.

<400> SEQUENCE: 3
cggtcattct gctgtgttcg taaaat                                              26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: comprising
      a sequence complementary to nucleotides 254-277 of the nucleotide
      sequence of V. parahaemolyticus TDH (Thermostable Direct
      Haemolysin) gene.
<221> NAME/KEY: modified_base
<222> LOCATION: (12)
<223> OTHER INFORMATION: a, t, c, or g

<400> SEQUENCE: 4
caggtactaa anggttgaca tcct                                                24
```